United States Patent [19]

Camaggi et al.

[11] Patent Number: 5,384,325
[45] Date of Patent: Jan. 24, 1995

[54] HETEROBICYCLIC DERIVATIVES WITH FUNGICIDAL ACTIVITY

[75] Inventors: Giovanni Camaggi, Novara; Lucio Filippini, San Donato Milanese; Marilena Gusmeroli, Monza; Raul Riva, Novara; Carlo Garavaglia, Cuggiono; Ernesto Signorini, Malnate; Mario Ferri, Milan, all of Italy

[73] Assignee: Isagro S.r.l., Milan, Italy

[21] Appl. No.: 232,745

[22] Filed: Apr. 25, 1994

[30] Foreign Application Priority Data

Apr. 27, 1993 [IT] Italy .................. MI 93/A/000819

[51] Int. Cl.⁶ .................. A61K 31/425; C07D 277/60
[52] U.S. Cl. ....................... 514/368; 548/154; 548/155
[58] Field of Search ............... 514/368; 548/154, 155

[56] References Cited

PUBLICATIONS

CA 110:114555e Preparation . . . Antibacterials. Veverka et al., p. 664, 1989.
CA 114:81341j New Thiazolo . . . Cephalosporins. Nam et al., p. 685, 1991.

*Primary Examiner*—Mary C. Lee
*Assistant Examiner*—Joseph K. McKane
*Attorney, Agent, or Firm*—George P. Hoare, Jr.

[57] ABSTRACT

Compounds based on heterobicyclic derivatives displaying fungicidal activity, having the general formula (I):

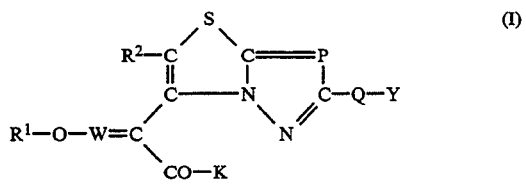

32 Claims, No Drawings

HETEROBICYCLIC DERIVATIVES WITH FUNGICIDAL ACTIVITY

The present invention relates to compounds based of heterobicyclic derivatives, displaying high antifungal activity, as well as to the process for preparing them.

Therefore, the subject-matter of the present invention are compounds based on heterobicyclic derivatives, having the general formula (I):

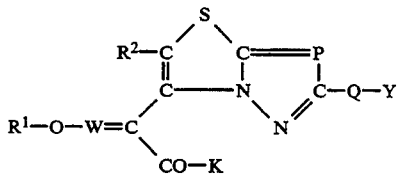

wherein:

P and W, which are the same or different from each other, represent a nitrogen atom, or a

moiety;

K represents —O—$R^4$ moiety, or an

moiety;

$R^1$ and $R^4$, which are the same or different from each other, represent a linear or branched $C_1$-$C_8$ alkyl or halo-alkyl group;

$R^2$, $R^3$, $R^5$ and $R^6$, which are the same or different from each other, represent a hydrogen atom or a linear or branched $C_1$-$C_8$ alkyl or haloalkyl group;

Q represents a direct bond; an oxygen atom; a linear or branched $C_1$-$C_8$ alkyl group; a linear or branched oxoalkyl moiety of the type:
—$(C_nH_{2n})$—O—;
—O—$(C_mH_{2m})$—;
a carbonylic group of

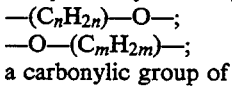

type;

Y represents a linear or branched $C_1$-$C_8$ alkyl group; a $C_3$-$C_6$ cycloalkylic group; a phenyl, naphthyl, five- or six-membered heterocyclic group containing from 1 to 3 heteroatoms selected from nitrogen, oxygen or sulfur, also fused with a benzene ring, all of them being optionally substituted with one or more of:
halogens, such as fluorine, chlorine, bromine, iodine;
linear or branched $C_1$-$C_6$ alkyl or haloalkyl groups;
linear or branched $C_1$-$C_6$ alkoxy or haloalkoxy groups;
nitrile groups;
linear or branched $C_2$-$C_8$ carboalkoxy or carbamoyl groups;
—(V)—Z groups in which:

Z represents a phenyl group, a $C_5$-$C_{10}$ heterocyclic group in which the heteroatoms are selected from oxygen, nitrogen or sulfur, optionally substituted with:
halogens, such as fluorine, chlorine, bromine, iodine;
linear or branched $C_1$-$C_6$ alkyl groups;
linear or branched $C_1$-$C_6$ alkoxy or haloalkoxy groups;
nitrile groups;

V represents an oxygen or sulfur atom, or a carbonylic group;

n and m, which are the same or different from each other, are an integer comprised within the range of from 0 to 6;

r is either zero or 1.

The structure of general formula (I) can display at least one (E)/(Z) isomerism. Taking into consideration both pure isomers of compounds of general formula (I), and mixtures thereof, falls within the scope of the present invention.

The compounds of general formula (I) are antifungal agents.

Examples of $R^1$, $R^2$, $R^3$, $R^4$, $R^5$ and $R^6$ radicals are: methyl, ethyl, isopropyl, trifluoromethyl, 2,2,2-trifluoroethyl, and so forth.

Examples of Y radicals are: methyl, isopropyl, tert.-butyl, 2-chlorophenyl, 3-chlorophenyl, 4-chlorophenyl, 2,4-dichlorophenyl, 4-bromophenyl, 2-trifluoromethylphenyl, 4-trifluoromethylphenyl, 3-benzoylphenyl, 4-benzoylphenyl, 2-fluorophenyl, 2,6-difluorophenyl, 2-methoxyphenyl, 4-methoxyphenyl, 3-butoxyphenyl, 4-(1,1,2,2-tetrafluoroethoxy)phenyl, 3-phenoxyphenyl, 4-phenoxyphenyl, 4-(4-chlorophenoxy)-phenyl, 2-cyanophenyl, pyrid-3-yl, 3-trifluoromethyl-pyrid-2-yl; thien-2-yl, 5-trifluoromethylthien-2-yl, 4-chloropyrimidin-2-yl, 4,6-dimethylpyrimidin-2-yl, 4-methyl-5-phenylthiazolyl, 6-chlorobenzoiso-oxazol-2-yl, and so forth.

Examples of Z radicals are: 2-chlorophenyl, 3-chlorophenyl, 4-chlorophenyl, 2,4-dichlorophenyl, 4-bromophenyl, 2-trifluoromethylphenyl 4-trifluoromethylphenyl, 3-benzoylphenyl, 4-benzoylphenyl, 2-fluorophenyl, 2,6-difluorophenyl, 2-methoxyphenyl, 4-methoxyphenyl, 3-butoxyphenyl,4-(1,1,2,2-tetrafluoroethoxy)phenyl, 3-phenoxyphenyl, 4-phenoxyphenyl, 4-(4-chlorophenoxy)phenyl, 2-cyanophenyl, pyrid-3-yl, 3-trifluoromethyl-pyrid-2-yl, thien-2-yl, 5-trifluoromethylthien-2-yl, 4-chloropyrimidin-2-yl, 4,6-dimethylpyrimidin-2-yl, 4-methyl-5-phenylthiazolyl, 6-chlorobenzoisooxazol-2-yl, and so forth.

Compounds of general formula (I) not illustrated in the examples, but which are equally interesting owing to their fungicidal activities, are:

(E)-2-(4-fluorophenyl)-5-(1-methoxycarbonyl-2-methoxyethen-1-yl)-6-methylthiazolo[3,2-b][1,2,4]triazole;

(E)-2-(4-fluorophenyl)-5-(1-dimethylamino-carbonyl-2-methoxyethen-1-yl)-6-methyl-thiazolo[3,2-b][1,2,4]triazole;

(E)-2-(4-fluorophenyl)-5-(1-methylaminocarbonyl-2-methoxyethen-1-yl)-6-methylthiazolo[3,2-b][1,2,4]triazole;

(E)-2-(2,4-difluorophenyl)-5-(1-methoxycarbonyl-2-methoxyethen-1-yl)-6-methylthiazolo[3,2-b][1,2,4]triazole;

(E)-2-(4-methylphenyl)-5-(1-methoxycarbonyl-2-methoxyethen-1-yl)-6-methylthiazolo[3,2-b][1,2,4]triazole;

(E)-2-(4-cyanophenyl)-5-(1-methoxycarbonyl-2-methoxyethen-1-yl)-6-methylthiazolo[3,2-b][1,2,4]triazole;

(E)-2-(4-methoxyphenyl)-5-(1-methoxycarbonyl-2-methoxyethen-1-yl)-6-methylthizaolo[3,2-b][1,2,4]triazole;

(E)-2-(2-methoxyphenyl)-5-(1-methoxycarbonyl-2-methoxyethen-1-yl)-6-methylthiazolo[3,2-b][1,2,4]triazole;

(E)-2-(3-trifluoromethylphenyl)-5-(1-methoxycarbonyl-2-methoxyethen-1-yl)-6-methylthiazolo[3,2-b][1,2,4]triazole;

(E)-2-[3-(4-chlorophenoxy)phenyl]-5-(1-methoxycarbonyl-2-methoxyethen-1-yl)-6-methylthiazolo[3,2-b][1,2,4]triazole;

(E)-2-(2,4-difluorophenyl)-5-(methoxyiminomethoxycarbonyl-methyl)-6-methylthiazolo[3,2-b][1,2,4]triazole;

(E)-2-(2-methylphenyl)-5-(methoxyiminomethoxycarbonyl-methyl)thiazolo[3,2-b][1,2,4]triazole;

(E)-2-[4-(4-chlorophenyl)thiazol-2-ylphenyl]-5-(1-methoxycarbonyl-2-methoxyethen-1-yl)-6-methylthiazolo[3,2-b][1,2,4]triazole;

(E)-2-(7-chlorobenzothiazol-2-ylphenyl)-5-(1-methoxycarbonyl-2-methoxyethen-1-yl)-6-methylthiazolo[3,2-b][1,2,4]triazole;

(E)-2-(5-trifluoromethylpyrid-3-yl)-5-(1-methoxycarbonyl-2-methoxyethen-1-yl)-6-methylthiazolo[3,2-b][1,2,4]triazole;

(E)-2-(4,6-dimethylpyrimidin-2-yl)-5-(1-methoxycarbonyl-2-methoxyethen-1-yl)-6-ethylthiazolo[3,2-b][1,2,4]triazole (E)-2-(naphth-2-yl)-5-(1-methoxycarbonyl-2-methoxyethen-1-yl)-6-methylthiazolo[3,2-b][1,2,4]triazole;

(E)-2-(naphth-2-yl)-5-(methoxyiminomethoxy-carbonyl-methyl)-6-methylthiazolo[3,2-b][1,2,4]triazole;

(E)-2-(thien-2-yl)-5-(1-methoxycarbonyl-2-methoxyethen-1-yl)-thiazolo[3,2-b][1,2,4]triazole;

(E)-2-(4-chlorobenzoyl)-5-(1-methoxycarbonyl-2-methoxyethen-1-yl)-6-methylthiazolo[3,2-b][1,2,4]triazole;

(E)-2-(3-trifluoromethylbenzoyl)-5-(1-methoxycarbonyl-2-methoxyethen-1-yl)-6-methylthiazolo-[3,2-b][1,2,4]triazole;

(E)-2-(4-trifluoromethylbenzoyl)-5-(methoxyiminomethoxycarbonyl-methyl)thiazolo[3,2-b][1,2,4]triazole;

(E)-2-(3-chloro-5-trifluoromethylpyridyl-2oxy)-5-(1-methoxycarbonyl-2-methoxyethen-1-yl)-6-methylthiazolo[3,2-b][1,2,4]triazole;

(E)-2-(3-chloro-5-trifluoromethylpyridyl-2-oxy)-5-(methoxyiminomethoxycarbonyl-methyl)-6-methylthiazolo[3,2-b][1,2,4]triazole;

(E)-2-(2-chlorobenzyloxy)-5-(1-methoxycarbonyl-2-methoxyethen-1-yl)-6-methylthiazolo[3,2-b][1,2,4]triazole;

(E)-2-[4-(2,2,1,1-tetrafluoroethoxy)benzyloxy]-5-(1-methoxycarbonyl-2-methoxyethen-1-yl)-6-methylthiazolo[3,2-b][1,2,4]triazole;

(E)-2-(2-cyanophenoxymethyl)-5-(1-methoxycarbonyl-2-methoxyethen-1-yl)-6-methylthiazolo[3,2-b][1,2,4]triazole;

(E)-2-[1-(4-chlorophenoxy)ethyl]-5-(1-methoxycarbonyl-2-methoxyethen-1-yl)-thiazolo-[3,2-b][1,2,4]triazole;

(E)-2-(1-(4-chlorophenoxy)ethyl)-5-(methoxyiminomethoxycarbonyl-methyl)-6-methylthiazolo[3,2-b][1,2,4]triazole;

(E)-2-[2-(4-trifluoromethylphenoxy)prop-2-yl]-5-(1-methoxycarbonyl-2-methoxyethen-1-yl)-6-methylthiazolo[3,2-b][1,2,4]triazole;

(E)-2-[2-(4-trifluoromethylphenoxy)prop-2-yl]-5-(methoxyiminomethoxycarbonyl-methyl)-6-methylthiazolo[3,2-b][1,2,4]triazole;

(E)-2-(tert.-butyl)-5-(methoxyiminomethoxycarbonyl-methyl)-6-methylthiazolo[3,2-b][1,2,4]triazole;

(E)-2-(1,1-dimethylpropyl)-5-(1-methoxycarbonyl-2-methoxyethen-1-yl)-6-methylthiazolo[3,2-b][1,2,4]triazole;

(E)-6-(4-chlorophenyl)-3-(1-methoxycarbonyl-2-methoxyethen-1-yl)pyrazolo[1,5-b]thiazole;

(E)-6-(4-chlorophenyl)-3-(1-methoxycarbonyl-2-methoxyethen-1-yl)-7-methylpirazolo[1,5-b]thiazole;

When W represents a $$a = \overset{|}{C} - R^3$$

moiety wherein $R^3$ has the same meaning as defined hereinabove, the compounds according to the present invention can be obtained by means of a process which comprises causing a compound having general formula (II):

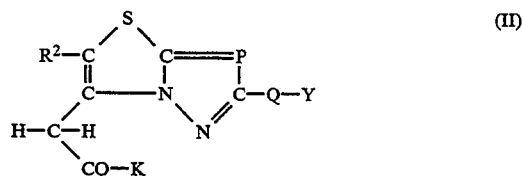

(II)

wherein $R^2$, P, Y, Q and K have the same meaning as defined hereinabove, to react with an alkyl ester having the general formula (III):

$$R^3\text{—}COOR^7 \qquad (III)$$

wherein $R^3$ has the same meaning as disclosed hereinabove and $R^7$ represents a $C_1$-$C_3$ alkyl group, in a dipolar protic or aprotic solvent such as, e.g., methyl alcohol, tert.-butyl alcohol, N,N-methylpyrrolidone, N-methylpyrrolidone, in the presence of a base such as, e.g., sodium hydride, potassium tert.-butoxide, at a temperature comprised within the range of from $-10°$ C. to $80°$ C., with the salt having the general formula (IV):

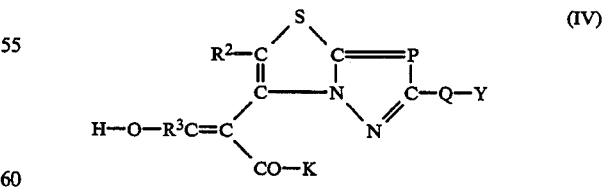

(IV)

being obtained from which, by reaction with a halogenating agent $R^1$—X, in which $R^1$ has the same meaning as defined hereinabove and X represents a halogen atom such as chlorine, bromine, iodine, or with an activated ester such as p-toluenesulfonate, at a temperature comprised within the range of from $-10°$ C. to $80°$ C. the desired compound having formula (Ia):

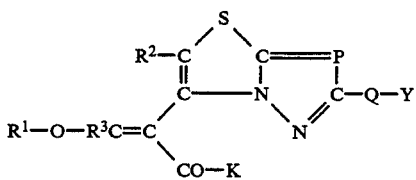 (Ia)

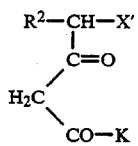 (VIII)

is obtained.

When W represents a hydrogen atom, the compounds according to the present invention can be obtained by means of a process which comprises causing a compound having the general formula (II) to react with an organic nitrite having the general formula (V):

 (V)

wherein $R^8$ represents a linear or branched $C_2$-$C_8$ alkyl group, in a dipolar protic or aprotic solvent such as, e.g., methyl alcohol, tetrahydrofurane, dioxane, in the presence of a base such as, e.g., sodium hydride, potassium tert.-butoxide, at a temperature comprised within the range of from −10° C. to 80° C., with the salt having the general formula (VI):

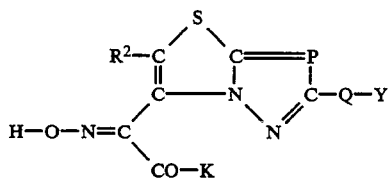 (VI)

being obtained from which, by reaction, with a halogenating agent $R^1$—X, wherein $R^1$ and X have the same meaning as defined hereinabove, under analogous conditions to those as disclosed above in order to transform the salt having the general formula (IV) into the compound of formula (Ia), the compound having the formula (Ib):

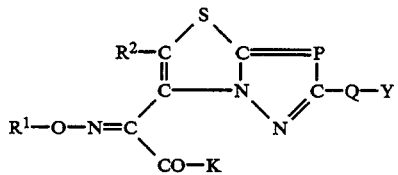 (Ib)

is obtained.

The compounds having the general formula (II) can be prepared by causing a compound having the general formula (VII):

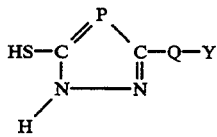 (VII)

wherein P, Q and Y have the same meaning as defined hereinabove, to react with a derivative of the gammahalo-beta-ketoalkanoic acid having the general formula (VIII):

wherein $R^2$ and K have the same meaning as disclosed hereinabove and X' is a chlorine or bromine atom. Such a reaction can be carried out, e.g., according to such a procedure as described in "Journal of Heterocyclic Chemistry" (1978), Volume 15, Page 401 or in "Journal of Heterocyclic Chemistry" (1980), Volume 17, Page 1321.

When P is a nitrogen atom, the compounds having the general formula (VII) can be prepared, e.g., according to the methodologies as reported in the references cited hereinabove.

When P represents a

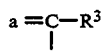

moiety in which $R^3$ has the meaning as defined hereinabove, the compounds having the general formula (VII) can be prepared, e.g., according to such methods as described by G. P. Ellis in "Synthesis of Fused Heterocycles" in Volume 47, Part 1, Page 575 of "The Chemistry of Heterocyclic Compounds" (1987).

The derivatives of the gamma-halo-betaketoalkanoic acid having the general formula (VIII) are commercial products, or they are easily prepared according to methodologies reported in technical Literature such as, e.g., by bromination of betaketoalkanoic acids, obtained by means of pyridinium perbromide.

The compounds having the general formula (I) display a particularly high fungicidal activity against fungal pathogens belonging to various genera.

They are particularly effective against phytopathogenic fungi which attack vine, sugar beet, cereal, Cucurbits crops and orchards. They can also be active as antimycotic agents such as, e.g., for controlling the pathogenic fungi belonging to Candida genus or Trichophytum genus.

The plant diseases which can be combatted with the compounds according to the present invention are, e.g., the following:

*Helminthosporium teres* on cereals;
*Erysiphe graminis* on cereals;
*Puccinia spp.* on cereals;
*Plasmopara viticola* on vine;
*Phytium* on horticultural species;
*Phytophthora spp.* on horticultural species;
*Septoria spp.* on cereals;
*Sphaerotheca fuliginea* on Cucurbits (e.g., cucumber);
*Rhynchosporium* on cereals;
*Podosphaera leucotricha* on apple;
*Uncinula necator* on vines;
*Venturia spp.* on fruit trees;
*Pyricularia oryzae* on rice;
*Botrytis cinerea*;
*Fusarium spp.* on cereals;
and so on.

When they are used for plant healing purposes, the compounds having the general formula (I) are capable of performing a fungicidal action of both curative and preventative character and, furthermore, display low or no phytotoxicity.

For practical uses in agriculture, it is often useful to have available fungicidal compositions containing, as their active substance, one or more compounds having general formula (I), possibly also as a mixture of isomers.

These compositions can be applied onto any portions of plants, e.g., on leaves, stems, branches and roots, or as seed dressing, before sowing, or also to the locus on which the plant grows.

The compositions can be used in forms of dry powders, wettable powders, emulsifiable concentrates, microemulsions, pastes, granular compositions, solutions, suspensions, and so forth: the choice of the type of composition will depend on the specific use envisaged.

The compositions are prepared according to known methodologies, e.g., by diluting or dissolving the active substance with a solvent means and/or a solid diluent, possibly in the presence of surfactants.

As solid diluents, or carriers, the following can be used: silica, kaolin, bentonite, talc, fossil meal, dolomite, calcium carbonate, magnesia, chalk, clays, synthetic silicates, attapulgite, sepiolite.

As liquid diluents, besides, of course, water, various types of solvents can be used, e.g., aromatics (xylenes or mixture of alkylbenzenes), chlorinated aromatics (chlorobenzene), paraffins (petroleum fractions), alcohols (methanol, propanol, butanol, octanol, glycerol), amines, amides (N,N'-dimethylformamide, N-methylpyrrolidone), ketones (acetone, cyclohexanone, acetophenone, isoforone, ethylamylketone), esters (isobutyl acetate).

As surfactants, there may be used sodium, calcium, triethanolamine or triethanolamine salts of alkylsulfates, alkylarylsulfonates, polyethoxy alkylphenols, fatty alcohols condensed with ethylene oxide, polyethoxy fatty acids, polyethoxy sorbitan esters, lignosulfonates.

The compositions may also contain special additives for particular purposes, such as, e.g., adhesion conferring agents, such as gum arabic, polyvinyl alcohol, polyvinylpyrrolidone.

If so desired, to the compositions according to the present invention also other compatible active substances can be added, such as fungicides, phytoregulants, antibiotics, herbicides, insecticides, fertilizers.

The concentration of active substance in the above said compositions may vary within a wide range, according to the active compound, the crop, the pathogen, the environmental conditions and the adopted formulation type.

In general, the concentration of active substance is comprised within the range of from 0.1 to 95%, preferably of from 0.5 to 90%.

The examples reported in the following, are supplied for merely illustrative purposes, and in no way shall they limit the scope of the present invention.

EXAMPLE 1

Preparation of
(E)-2-(4-chlorophenyl)-5-(1-methoxycarbonyl-2-methoxyethen-1-yl)-6-methylthiazolo[3,2-b][1,2,4]triazole Compound No. 1.

Under a blanketing nitrogen atmosphere, 0.23 g of sodium hydride at 80% (w/w) in paraffin is dispersed in 5 cm³ of anhydrous dimethylformamide (DMF).

Thereafter, 1.2 g of 2-(4-chlorophenyl)-5-(methoxycarbonyl methyl)-6-methylthiazolo[3,2-b][1,2,4]triazole in 2.5 cm³ of methyl formate and 5 cm³ of anhydrous dimethylformamide (DMF) are added dropwise during 40 minutes.

The resulting mixture is kept 4 hours at room temperature.

The reaction mixture is cooled down to 5° C. and 2.5 cm³ of methyl iodide (CH₃I) is added.

The resulting solution is kept overnight at room temperature and subsequently is diluted with water and extracted with ethyl acetate.

The organic phase is washed with brine, thoroughly desiccated over sodium sulfate and concentrated under reduced pressure.

The so obtained raw product is purified by silica gel chromatography, eluting with 7:3 hexane:ethyl acetate.

0.75 g of Compound No. 1, the NMR spectroscopic data of which are reported in Table 1, is obtained, in a yield of 55%.

EXAMPLE 2

Preparation of
(E)-2-(4-chlorophenyl)-5-(methoxyiminomethoxycarbonylmethyl)-6-methylthiazolo[3,2-b][1,2,4]triazole Compound No. 2

Under a blanketing nitrogen atmosphere, 0.25 g of sodium hydride at 80% (w/w) in paraffin is dispersed in 5 cm³ of anhydrous dioxane.

Thereafter, 1.15 g of 2-(4-chlorophenyl)-5-(methoxycarbonylmethyl)-6-methylthiazolo[3,2-b][1,2,4]triazole and 9 g of amyl nitrile in 10 cm³ of anhydrous dioxane are added dropwise during a 30-minute time.

The resulting mixture is kept at room temperature for 48 hours and is subsequently heated at 40° C. for 4 hours.

The reaction mixture is cooled down to 5° C. and 2.5 cm³ of methyl iodide (CH₃I) is added.

The resulting solution is kept overnight at room temperature and subsequently is diluted with water and extracted with ethyl acetate.

The organic phase is washed with brine, thoroughly desiccated over sodium sulfate and concentrated under reduced pressure.

The so obtained raw product is purified by silica gel chromatography, eluting with 7:3 hexane:ethyl acetate.

0.50 g of Compound No. 2, the NMR spectroscopic data of which are reported in Table 1, is obtained, in a yield of 38%.

EXAMPLES 3–25

By operating analogously to examples 1 and 2, the compound Nos. 3–25 were prepared.

Compound No. 1

(E)-2-(4-chlorophenyl)-5-(1-methoxycarbonyl-2-methoxyethen-1-yl)-6-methylthiazolo[3,2-b][1,2,4]triazole;

Compound No. 2

(E)-2-(4-chlorophenyl)-5-(methoxyiminomethoxycarbonylmethyl)-6-methylthiazolo[3,2-b][1,2,4]triazole;

Compound No. 3

(E)-2-(4-trifluoromethylphenyl)-5-(1-methoxycarbonyl-2-methoxyethen-1-yl)-6-methylthiazolo[3,2-b][1,2,4]triazole;

Compound No. 4

(E)-2-(4-trifluoromethylphenyl)-5-(methoxyiminomethoxycarbonyl-methyl)-6-methylthiazolo[3,2-b][1,2,4]triazole;

Compound No. 5

(E)-2-(4-benzoylphenyl)-5-(1-methoxycarbonyl-2-methoxyethen-1-yl)-6-methylthiazolo[3,2-b][1,2,4]triazole;

Compound No. 6

(E)-2-(2-chlorophenyl)-5-(1-methoxycarbonyl-2-methoxyethen-1-yl)-6-methylthiazolo[3,2-b][1,2,4]triazole;

Compound No. 7

(E)-2-(4-chlorophenyl)-5-(1-methoxycarbonyl-2-methoxyethen-1-yl)-thiazolo[3,2-b][1,2,4]triazole.

Compound No. 8

(E)-6-methyl-5-(1-methoxycarbonyl-2-methoxyethen-1-yl)-3-(4-methoxyphenyl)thiazolo[3,2-b][1,2,4]triazole.

Compound No. 9

(E)-6-trifluoromethyl-5-(1-methoxycarbonyl-2-methoxyethen-1-yl)-3-(4-methoxyphenyl)thiazolo[3,2-b][1,2,4]triazole.

Compound No. 10

(E)-6-methyl-5-(1-methoxycarbonyl-2-methoxyethen-1-yl)-3-(4-cyclopropylmethoxyphenyl)-thiazolo[3,2-b][1,2,4]triazole.

Compound No. 11

(E)-6-methyl-5-(1-methoxycarbonyl-2-methoxyethen-1-yl)-3-(4-benzyloxyphenyl)thiazolo[3,2-b][1,2,4]triazole.

Compound No. 12

(E)-6-methyl-5-(1-methoxycarbonyl-2-methoxyethen-1-yl)-3-(2-methoxyphenyl)thiazolo[3,2-b][1,2,4]triazole.

Compound No. 13

(E)-6-methyl-5-(1-methoxycarbonyl-2-methoxyethen-1-yl)-3-(4-phenoxyphenyl)thiazolo[3,2-b][1,2,4]triazole.

Compound No. 14

(E)-6-methyl-5-(1-methoxycarbonyl-2-methoxyethen-1-yl)-3-(2-methylprop-2-yl)thiazolo[3,2-b][1,2,4]triazole.

Compound No. 15

(E)-6-methyl-5-(1-methoxycarbonyl-2-methoxyethen-1-yl)-3-(prop-2-yl)thiazolo[3,2-b][1,2,4]triazole.

Compound No. 16

(E)-6-methyl-5-(1-methoxycarbonyl-2-methoxyethen-1-yl)-3-(cyclohexyl)thiazolo[3,2-b][1,2,4]triazole.

Compound No. 17

(E)-6-methyl-5-(1-methoxycarbonyl-2-methoxyethen-1-yl)-3-(2-methylphenyl)thiazolo[3,2-b][1,2,4]triazole.

Compound No. 18

(E)-6-methyl-5-(1-methoxycarbonyl-2-methoxyethen-1-yl)-3-(2-fluorophenyl)thiazolo[3,2-b][1,2,4]triazole.

Compound No. 19

(E)-6-methyl-5-(1-methoxycarbonyl-2-methoxyethen-1-yl)-3-(2,6-difluorophenyl)thiazolo[3,2-b][1,2,4]triazole.

Compound No. 20

(E)-6-methyl-5-(1-methoxycarbonyl-2-methoxyethen-1-yl)-3-[5-(4-chlorophenyl)isooxazol-3-yl]thiazolo[3,2-b][1,2,4]triazole.

Compound No. 21

(E)-6-methyl-5-(1-methoxycarbonyl-2-methoxyethen-1-yl)-3-[(5-trifluoromethylpyridyl-2-oxy)phenyl]-thiazolo[3,2-b][1,2,4]triazole.

Compound No. 22

(E)-6-methyl-5-(1-methoxycarbonyl-2-methoxyethen-1-yl)-3-[4-(4-chlorophenyl)thiazol-2-yl]thiazolo[3,2-b][1,2,4]triazole.

Compound No. 23

(E)-6-methyl-5-(1-methoxycarbonyl-2-methoxyethen-1-yl)-3-(2,2-dimethylprop-1-yl)thiazolo[3,2-b][1,2,4]-triazole.

Compound No. 24

(E)-6-methyl-5-(1-methoxycarbonyl-2-methoxyethen-1-yl)-3-(2-naphthyl)thiazolo[3,2-b][1,2,4]triazole.

Compound No. 25

(E)-6-methyl-5-(1-methoxycarbonyl-2-methoxyethen-1-yl)-3-[5-(2-methylprop-2-yl)isooxazol-3-yl]thiazolo-[3,2-b][1,2,4]triazole.

The respective NMR spectroscopic data are reported in Table 1.

EXAMPLE 26

Determination of preventative fungicidal activity against cucurbits powdery mildew (*Sphaerotheca fuliginea*).

Leaves of plants of cucumber, Marketer cultivar, grown in pots in a conditioned environment (20°±1° C., R.H. 70%), were treated by spraying the compound Nos. 1–25 in water-acetone solution at 20% acetone by volume, onto both of their faces.

After a 24-hour stay in conditioned environment, an aqueous suspension of conidia of *Sphaerotheca fuliginea* (200000 conidia per cm$^3$) was sprayed onto both faces of plant leaves.

The plants were then kept in a saturated humidity environment, at 21° C., throughout the fungus incubation time.

At the end of said time period (8 days), the fungicidal activity was evaluated according to a percent evaluation scale ranging from 100 (healthy plant) to 0 (completely infected plant).

All synthetized compounds demonstrated an infection control of >90, at the concentration of 500 ppm.

EXAMPLE 27

Determination of preventative fungicidal activity against net blotch of barley (*Elminthosporium teres*)

Leaves of plants of barley, Arna cultivar, grown in pots in a conditioned environment (20°±1° C., R.H. 70%), were treated by spraying the compound Nos. 1-25 in water-acetone solution at 20% acetone by volume, onto both of their faces.

After a 24-hour stay in conditioned environment, an aqueous suspension of conidia of *Elminthosporium teres* (250,000 conidia per $cm^3$) was sprayed onto both faces of plant leaves.

The plants were kept in a saturated humidity environment, at 21° C., throughout the fungus incubation time.

At the end of said time period (12 days), the fungicidal activity was evaluated according to a percent evaluation scale ranging from 100 (healthy plant) to 0 (completely infected plant).

All synthetized compounds demonstrated an infection control of >90, at the concentration of 500 ppm.

EXAMPLE 28

Determination of preventative fungicidal activity against downy mildew of vines (*Plasmopara viticola*)

Leaves of plants of vines, Dolcetto cultivar, grown in pots in a conditioned environment (20°±1° C., R.H. 70%), were treated by spraying the compound Nos. 1-25 in water-acetone solution at 20% acetone by volume on both of their faces.

After a 24-hour stay in conditioned environment, an aqueous suspension of conidia of *Plasmopara viticola* (200,000 conidia per $cm^3$) was sprayed onto both faces of plant leaves.

The plants were kept in a saturated humidity environment, at 21° C., throughout the fungus incubation time.

At the end of said time period (7 days), the fungicidal activity was evaluated according to a percent evaluation scale ranging from 100 (healthy plant) to 0 (completely infected plant).

All synthetized compounds demonstrated an infection control of >90, at the concentration of 500 ppm.

TABLE 1

| Compound | N.M.R. spectroscopic data (60 MHz, $CDCl_3$) |
|---|---|
| 1 | 2,3 (3H, s); 3,8 (3H, s); 4,0 (3H, s); 7,3 (2H, m); 7,9 (2H, m); 8,1 (1H, s). |
| 2 | 2,3 (3H, s); 3,7 (3H, s); 4,1 (3H, s); 7,3 (2H, m); 7,9 (2H, m). |
| 3 | 2,4 (3H, s); 3,8 (3H, s); 4,0 (3H, s); 7,8 (2H, m); 8,3 (2H, m); 8,1 (1H, s). |
| 4 | 2,4 (3H, s); 3,7 (3H, s); 4,1 (3H, s); 7,8 (2H, m); 8,3 (2H, m). |
| 5 | 2,3 (3H, s); 3,8 (3H, s); 4,0 (3H, s); 7,8 (9H, m); 8,1 (1H, s). |
| 6 | 2,3 (3H, s); 3,8 (3H, s); 4,0 (3H, s); 7,4 (3H, m); 7,9 (1H, m); 8,1 (1H, s). |
| 7 | 3,8 (3H, s); 4,1 (3H, s); 7,1 (1H, s); 7,4 (2H, m); 8,0 (2H, m); 8,1 (1H, s). |
| 8 | 2,2 (3H, s); 3,7 (3H, s); 3.8 (3H, s); 3,9 (3H, s); 6.9 (2H, d); 7.7 (1H, s); 8.1 (2H, d). |
| 9 | 3.7 (3H, s); 3.8 (3H, s); 4.0 (3H, s); 7.0 (2H, d); 7.8 (1H, s); 8.1 (2H, d). |
| 10 | 0.4 (4H, m); 1.0 (1H, m); 2.3 (3H, s) 3.5 (3H, s); 3.6 (2H, d); 3.8 (3H, s) 6.7 (2H, d); 7.6 (1H, s); 7.8 (2H,d). |
| 11 | 2.3 (3H, s); 3.7 (3H, s); 3.9 (3H, s); 5.1 (2H, s); 7.0 (2H, d); 7.4 (5H, s); |

TABLE 1-continued

| Compound | N.M.R. spectroscopic data (60 MHz, $CDCl_3$) |
|---|---|
| | 7.8 (1H, s); 8.0 (2H, d). |
| 12 | 2.3 (3H, s); 3.7 (3H, s); 3.8 (3H, s); 3.9 (3H, s); 7.1 (3H, m); 7.7 (1H, s); 7.8 (1H, m). |
| 13 | 2.2 (3H, s); 3.8 (3H, s); 4.0 (3H, s); 6.9 (7H, m); 7.6 (2H, d); 7.8 (1H, s). |
| 14 | 1.3 (9H, s); 2.1 (3H, s); 3.6 (3H, s); 3.8 (3H, s); 7.6 (1H, s). |
| 15 | 1.3 (6H, d); 2.3 (3H, s); 3.1 (1H, m); 3.6 (3H, s); 3.8 (3H, s); 7.7 (1H, s). |
| 16 | 1.1 (10H,m); 2.2 (3H, s); 2.9 (1H, m); 3.6 (3H, s); 3.8 (3H, s); 7.6 (1H, s). |
| 17 | 2.4 (3H, s); 2.6 (3H, s); 3.8 (3H, s); 4.0 (3H, s); 7.3 (3H, m); 7.9 (1H, s); 8.1 (1H, m). |
| 18 | 2.4 (3H, s); 3.8 (3H, s); 4.0 (3H, s); 7.3 (4H, m); 7.9 (1H, s). |
| 19 | 2.5 (3H, s); 3.8 (3H, s); 4.0 (3H, s); 7.2 (3H, m); 7.9 (1H, s). |
| 20 | 2.2 (3H, s); 3.6 (3H, s); 3.8 (3H, s); 6.6 (1H, s); 7.4 (2H, m); 7.6 (1H, s); 7.7 (2H, m). |
| 21 | 2.3 (3H, s); 3.7 (3H, s); 4.0 (3H, s); 7.1 (3H, m); 7.8 (1H, s); 8.2 (4H, m). |
| 22 | 2.2 (3H, s); 3.7 (3H, s); 3.9 (3H, s); 7.2 (1H, d); 7.3 (2H, m); 7.7 (1H, s); 7.8 (2H, m). |
| 23 | 1.2 (9H, s); 2.1 (3H, s); 2.7 (2H, s); 3.6 (3H, s); 3.8 (3H, s); 7.6 (1H, s). |
| 24 | 2.2 (3H, s); 3.7 (3H, s); 3.9 (3H, s); 7.4 (6H, m); 7.7 (1H, s); 8.1 (1H, m); 8.1 (2H, d). |
| 25 | 1.4 (9H, s); 3.6 (3H, s); 3.8 (3H, s); 6.1 (1H, s); 7.7 (1H, s). |

We claim:

1. Compounds based on heterobicyclic derivatives, having the general formula (I):

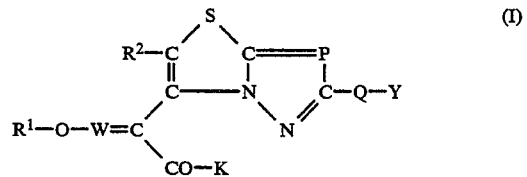

wherein:

P and W, which are the same or different from each other, represent a nitrogen atom, or a

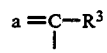

moiety;

K represents an —O—$R^4$ moiety, or an

moiety;

$R^1$ and $R^4$, which are the same or different from each other, represent a linear or branched $C_1$-$C_8$ alkyl or halo-alkyl group;

$R^2$, $R^3$, $R^5$ and $R^6$, which are the same or different from each other, represent a hydrogen atom or a linear or branched $C_1$-$C_8$ alkyl or haloalkyl group;

Q represents a direct bond; an oxygen atom; a linear or branched $C_1$-$C_8$ alkyl group; a linear or branched oxoalkyl moiety of the type:
—($C_nH_{2n}$)—O—;
—O—($C_mH_{2m}$)—; a carbonylic group of $$-\overset{\overset{O}{\|}}{C}-$$

type;

Y represents a linear or branched $C_1$-$C_8$ alkyl group; a $C_3$-$C_6$ cycloalkylic group; a phenyl, naphthyl, a five- or six-membered heterocyclic group containing from 1 to 3 heteroatoms selected from nitrogen, oxygen or sulfur, also fused with a benzene ring, all of them being optionally substituted with one or more of:

halogens, such as fluorine, chlorine, bromine, iodine;
linear or branched $C_1$-$C_6$ alkyl or haloalkyl groups;
linear or branched $C_1$-$C_6$ alkoxy or haloalkoxy groups;
nitrile groups;
linear or branched $C_2$-$C_8$ carboalkoxy or carbamoyl groups;
—(V)$_r$—Z groups in which:
  Z represents a phenyl group, a $C_5$-$C_{10}$ heterocyclic group in which the heteroatoms are selected from oxygen, nitrogen or sulfur, optionally substituted with:
    halogens, such as fluorine, chlorine, bromine, iodine;
    linear or branched $C_1$-$C_6$ alkyl groups;
    linear or branched $C_1$-$C_6$ alkoxy or haloalkoxy groups;
    nitrile groups;
  V represents an oxygen or sulfur atom, or a carbonylic group;
  n and m, which are the same or different from each other, are an integer comprised within the range of from 0 to 6;
  r is either zero or 1.

2. Antifungal agents constituted by compounds based on heterobicyclic derivatives, having the general formula (I):

wherein:

P and W, which are the same or different from each other, represent a nitrogen atom, or a a =C—R$^3$ moiety;

K represents an —O—R$^4$ moiety, or an $$-\underset{\underset{R^6}{|}}{N}-R^5$$

moiety;

R$^1$ and R$^4$, which are the same or different from each other, represent a linear or branched $C_1$-$C_8$ alkyl or halo-alkyl group;

R$^2$, R$^3$, R$^5$ and R$^6$, which are the same or different from each other, represent a hydrogen atom or a linear or branched $C_1$-$C_8$ alkyl or haloalkyl group;

Q represents a direct bond; an oxygen atom; a linear or branched $C_1$-$C_8$ alkyl group; a linear or branched oxoalkyl moiety of the type:
—($C_nH_{2n}$)—O—;
—O—($C_mH_{2m}$)—;
a carbonylic group of the type $$-\overset{\overset{O}{\|}}{C}-;$$

Y represents a linear or branched $C_1$-$C_8$ alkyl group; a $C_3$-$C_6$ cycloalkylic group; a phenyl, naphthyl, a five- or six-membered heterocyclic group containing from 1 to 3 heteroatoms selected from nitrogen, oxygen or sulfur, also fused with a benzene ring, all of them being optionally substituted with one or more of:

halogens, such as fluorine, chlorine, bromine, iodine;
linear or branched $C_1$-$C_6$ alkyl or haloalkyl groups;
linear or branched $C_1$-$C_6$ alkoxy or haloalkoxy groups;
nitrile groups;
linear or branched $C_2$-$C_8$ carboalkoxy or carbamoyl groups;
—(V)$_r$—Z groups in which:
  Z represents a phenyl group, a $C_5$-$C_{10}$ heterocyclic group in which the heteroatoms are selected from oxygen, nitrogen or sulfur, optionally substituted with:
    halogens, such as fluorine, chlorine, bromine, iodine;
    linear or branched $C_1$-$C_6$ alkyl groups;
    linear or branched $C_1$-$C_6$ alkoxy or haloalkoxy groups;
    nitrile groups;
  V represents an oxygen or sulfur atom, or a carbonylic group;
  n and m, which are the same or different from each other, are an integer comprised within the range of from 0 to 6;
  r is either zero or 1.

3. Antifungal agents according to claim 2, in which R$^1$, R$^2$, R$^3$, R$^4$, R$^5$ and R$^6$ are; methyl, ethyl, isopropyl, trifluoromethyl, 2,2,2-trifluoroethyl.

4. Antifungal agents according to claim 2, in which Y is: methyl, isopropyl, tert.-butyl, 2-chlorophenyl, 3-chlorophenyl, 4-chlorophenyl, 2,4-dichlorophenyl, 4-bromophenyl, 2-trifluoromethylphenyl, 4-trifluoromethylphenyl, 3-benzoylphenyl, 4-benzoylphenyl, 2-fluorophenyl, 2,6-difluorophenyl, 2-methoxyphenyl, 4-methoxyphenyl, 3-butoxyphenyl, 4-(1,1,2,2-tetrafluoroethoxy)phenyl, 3-phenoxyphenyl, 4-phenoxyphenyl, 4-(4-chlorophenoxy)-phenyl, 2-cyanophenyl, pyrid-3-yl, 3-trifluoromethyl-pyrid-2-yl; thien-2-yl, 5-trifluoromethylthien-2-yl, 4-chloropyrimidin-2-yl, 4,6-dimethylpyrimidin-2-yl, 4-methyl-5-phenylthiazolyl, 6-chlorobenzoisooxazol-2-yl.

5. Antifungal agent according to claim 2, in which Z is: 2-chlorophenyl, 3-chlorophenyl, 4-chlorophenyl, 2,4-dichlorophenyl, 4-bromophenyl, 2-trifluoromethylphenyl, 4-trifluoromethylphenyl, 3-benzoylphenyl, 4-benzoylphenyl, 2-fluorophenyl, 2,6-difluorophenyl, 2-methoxyphenyl, 4-methoxyphenyl, 3-butoxyphenyl, 4-(1,1,2,2-tetrafluoroethoxy)phenyl, 3-phenoxyphenyl, 4-phenoxyphenyl, 4-(4-chlorophenoxy)phenyl, 2-cyanophenyl, pyrid-3-yl, 3-trifluoromethylpyrid-2-yl, thien-2-yl, 5-trifluoromethylthien-2-yl, 4-chloropyrimidin-2-yl, 4,6-dimethylpyrimidin-2-yl, 4-methyl-5-phenylthiazolyl, 6-chlorobenzoisooxazol-2-yl.

6. Antifungal agent according to claim 2, constituted by (E)-2-(4-chlorophenyl)-5-(1-methoxycarbonyl-2-methoxyethen-1-yl)-6-methylthiazolo[3,2-b][1,2,4]triazole.

7. Antifungal agent according to claim 2, constituted by (E)-2-(4-chlorophenyl)-5-(methoxyiminomethoxycarbonylmethyl)-6-methylthiazolo[3,2-b][1,2,4]triazole.

8. Antifungal agent according to claim 2, constituted by (E)-2-(4-trifluoromethylphenyl)-5-(1-methoxycarbonyl-2-methoxyethen-1-yl)-6-methylthiazolo[3,2-b][1,2,4]triazole.

9. Antifungal agent according to claim 2, constituted by (E)-2-(4-trifluoromethylphenyl)-5-(methoxyiminomethoxycarbonyl-methyl)-6-methylthiazolo[3,2-b][1,2,4]triazole.

10. Antifungal agent according to claim 2, constituted by (E)-2-(4-benzoylphenyl)-5-(1-methoxycarbonyl-2-methoxyethen-1-yl)-6-methylthiazol[3,2-b][1,2,4]triazole.

11. Antifungal agent according to claim 2, constituted by (E)-2-(2-chlorophenyl)-5-(1-methoxycarbonyl-2-methoxyethen-1-yl)-6-methylthiazolo[3,2-b[]1,2,4]triazole.

12. Antifungal agent according to claim 2, constituted by (E)-2-(4-chlorophenyl)-5-(1-methoxycarbonyl-2-methoxyethen-1-yl)-6-methyl-thiazolo-[3,2-b][1,2,4]triazole.

13. Antifungal agent according to claim 2, constituted by (E)-6-methyl-5-(1-methoxycarbonyl-2-methoxyethen-1-yl)-3-(4-methoxyphenyl)-thiazolo[3,2-b][1,2,4]triazole.

14. Antifungal agent according to claim 2, constituted by (E)-6-trifluoromethyl-5-(1-methoxycarbonyl-2-methoxyethen-1-yl)-3-(4-methoxyphenyl)thiazolo[3,2-b][1,2,4]triazole.

15. Antifungal agent according to claim 2, constituted by (E)-6-methyl-5-(1-methoxycarbonyl-2-methoxyethen-1-yl)-3-(4-cyclopropylmethoxyphenyl)-thiazolo[3,2-b]-[1,2,4]triazole.

16. Antifungal agent according to claim 2, constituted by (E)-6-methyl-5-(1-methoxycarbonyl-2-methoxyethen-1-yl)-3-(4-benzyloxyphenyl)thiazolo[3,2-b][1,2,4]-triazole.

17. Antifungal agent according to claim 2, constituted by (E)-6-methyl-5-(1-methoxycarbonyl-2-methoxyethen-1-yl)-3-(2-methoxyphenyl)thiazolo[3,2-b][1,2,4]triazole.

18. Antifungal agent according to claim 2, constituted by (E)-6-methyl-5-(1-methoxycarbonyl-2-methoxyethen-1-yl)-3-(4-phenoxyphenyl)thiazolo[3,2-b][1,2,4]triazole.

19. Antifungal agent according to claim 2, constituted by (E)-6-methyl-5-(1-methoxycarbonyl-2-methoxyethen-1-yl)-3-(2-methylprop-2-yl)thiazolo[3,2-b][1,2,4]-triazole.

20. Antifungal agent according to claim 2, constituted by (E)-6-methyl-5-(1-methoxycarbonyl-2-methoxyethen-1-yl)-3-(prop-2-yl)thiazolo[3,2-b][1,2,4]triazole.

21. Antifungal agent according to claim 2, constituted by (E)-6-methyl-5-(1-methoxycarbonyl-2-methoxyethen-1-yl)-3-(cyclohexyl)thiazolo[3,2-b][1,2,4]triazole.

22. Antifungal agent according to claim 2, constituted by (E)-6-methyl-5-(1-methoxycarbonyl-2-methoxyethen-1-yl)-3-(2-methylphenyl)thiazolo[3,2-b][1,2,4]triazole.

23. Antifungal agent according to claim 2, constituted by (E)-6-methyl-5-(1-methoxycarbonyl-2-methoxyethen-1-yl)-3-(2-fluorophenyl)thiazolo[3,2-b][1,2,4]triazole.

24. Antifungal agent according to claim 2, constituted by (E)-6-methyl-5-(1-methoxycarbonyl-2-methoxyethen-1-yl)-3-(2,6-difluorophenyl)thiazolo[3,2-b][1,2,4]-triazole.

25. Antifungal agent according to claim 2, constituted by (E)-6-methyl-5-(1-methoxycarbonyl-2-methoxyethen-1-yl)-3-[5-(4-chlorophenyl)isooxazol-3-yl]thiazolo[3,2-b][1,2,4]triazole.

26. Antifungal agent according to claim 2, constituted by (E)-6-methyl-5-(1-methoxycarbonyl-2-methoxyethen-1-yl)-3-[(5-trifluoromethylpyridyl-2-oxy)phenyl]thiazolo[3,2-b][1,2,4]triazole.

27. Antifungal agent according to claim 2, constituted by (E)-6-methyl-5-(1-methoxycarbonyl-2-methoxyethen-1-yl)-3-[4-(4-chlorophenyl)thiazol-2-yl]thiazolo[3,2-b][1,2,4]triazole.

28. Antifungal agent according to claim 2, constituted by (E)-6-methyl-5-(1-methoxycarbonyl-2-methoxyethen-1-yl)-3-(2,2-dimethylprop-1-yl)thiazolo[3,2-b][1,2,4]-triazole.

29. Antifungal agent according to claim 2, constituted by (E)-6-methyl-5-(1-methoxycarbonyl-2-methoxyethen-1-yl)-3-(2-naphthyl)thiazolo[3,2-b][1,2,4]triazole.

30. Antifungal agent according to claim 2, constituted by (E)-6-methyl-5-(1-methoxycarbonyl-2-methoxyethen-1-yl)-3-[5-(2-methylprop-2-yl)isooxazol-3-yl]thiazolo-[3,2-b][1,2,4]triazole.

31. Fungicidal compositions containing one or more compounds according to claim 2, either alone or in the presence of solid carriers, liquid extenders, surface active agents or other active principles.

32. Method for combatting the fungal infections consisting in applying to the plants, leaves, stams, branches and roots, and to the same seeds before sowing, or to the locus of the plant, fungicidal compositions according to claim 31.

* * * * *